United States Patent
Bhattacharyya et al.

(10) Patent No.: US 10,253,353 B2
(45) Date of Patent: Apr. 9, 2019

(54) ENHANCED METHODS OF RIBONUCLEIC ACID HYBRIDIZATION

(71) Applicants: THE BROAD INSTITUTE, INC., Cambridge, MA (US); THE GENERAL HOSPITAL CORPORATION, Boston, MA (US)

(72) Inventors: Roby Bhattacharyya, Cambridge, MA (US); Deborah Hung, Cambridge, MA (US); Milesh Patel, Jersey City, NJ (US)

(73) Assignees: The Broad Institute, Inc., Cambridge, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 15/101,676

(22) PCT Filed: Dec. 5, 2014

(86) PCT No.: PCT/US2014/068835
§ 371 (c)(1),
(2) Date: Jun. 3, 2016

(87) PCT Pub. No.: WO2015/085194
PCT Pub. Date: Jun. 11, 2015

(65) Prior Publication Data
US 2016/0304942 A1    Oct. 20, 2016

Related U.S. Application Data

(60) Provisional application No. 61/913,105, filed on Dec. 6, 2013.

(51) Int. Cl.
*C12Q 1/68* (2018.01)
*C07H 21/04* (2006.01)
*C12Q 1/6832* (2018.01)

(52) U.S. Cl.
CPC ................ *C12Q 1/6832* (2013.01)

(58) Field of Classification Search
None
See application file for complete search history.

(56) References Cited

U.S. PATENT DOCUMENTS 5,376,529 A    12/1994 Van Ness et al.
5,573,915 A *  11/1996 Barry, III ............ C07K 14/35
                                                     435/183
7,264,932 B2    9/2007 Latham et al.
7,465,562 B2   12/2008 Wangh et al.
2003/0039974 A1    2/2003 Skouv
2013/0023655 A1 *   1/2013 Fabis ............... C12N 15/1003
                                                     536/23.1

FOREIGN PATENT DOCUMENTS

WO      2006085906 A2    8/2006

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Archaea," Wikipedia.com (accessed May 11, 2016).*
"Algae," Wikipedia.com (accessed Mar. 4, 2016).*
"Protozoa," Wikipedia.com (accessed May 11, 2016).*
"List of sequenced bacterial genomes" (Wikipedia.com; accessed Jan. 24, 2014).*
International Search Report and Written Opinion for International Patent Application No. PCT/US2014/068835, dated Jan. 24, 2015, 13 pages.
International Preliminary Report on Patentability dated Jun. 16, 2016 for PCT/US2014/068835, Jun. 16, 2016, 7 pages.

* cited by examiner

*Primary Examiner* — Bradley L. Sisson
(74) *Attorney, Agent, or Firm* — Johnson, Marcou & Isaacs, LLC

(57) ABSTRACT

This disclosure relates to a method for increasing the hybridization efficiency of a probe and a target RNA in a sample, for example to identify a particular RNA present in the sample. The method includes heating a lysate sample comprising at least one target RNA, such as a tRNA, mRNA or rRNA, at a temperature of about 95° C. for a time sufficient to interfere with secondary structure of the RNA, wherein the time is short enough, such that the RNA in the cell lysate sample are not significantly degraded, and wherein the lysate comprises a cell lysis buffer comprising a chemical denaturant. To detect a target RNA in the lysate, the lysate is contacted with at least one detectable probe, such as a labeled probe, designed to specifically hybridize to the target RNA in the lysate.

29 Claims, 5 Drawing Sheets

ENHANCED METHODS OF RIBONUCLEIC ACID HYBRIDIZATION

CROSS REFERENCE TO RELATED APPLICATIONS

This application is a 35 U.S.C. § 371 national stage of International Application No. PCT/US14/68835 filed on Dec. 5, 2014, and published in English under PCT Article 21(2), which claims the benefit of U.S. Provisional Application No. 61/913,105, filed Dec. 6, 2013. The entire contents of the above-identified priority applications are hereby fully incorporated herein by reference.

FEDERALLY SPONSORED RESEARCH OR DEVELOPMENT

This invention was made with Government support under Grant number HHSN272200900018C awarded by the National Institutes of Health. The Government has certain rights in the invention.

FIELD OF THE INVENTION

The present disclosure relates generally to an improved method of hybridization-based identification of ribonucleic acid (RNA) in a cell lysate.

BACKGROUND OF THE INVENTION

Identification of pathogenic organisms, for example in a subject or the food supply, is a key first step in devising an informed, effective treatment strategy or protection of the food supply, respectively. For example, to effectively treat pathogen infection, it is advisable to begin treatment as early as possible in the in the development of the infection, ideally even before onset of severe clinical symptoms. Similarly, protection of the food supply may require early action to detect contamination with pathogenic organisms and effectively remove tainted or otherwise contaminated food from distribution channels, before large scale outbreaks of food poisoning.

Currently, microbiologic methods rely on growth of pathogens in culture, followed by subculture and biochemical assays to determine pathogen identity, a process that can take over 48 hours. Current efforts at molecular diagnostics have centered on DNA recognition through PCR amplification, or recognition of protein signatures through mass spectrometry. PCR-based techniques have the advantage of amplification of signal, potentially permitting earlier detection. However, polymerases used in PCR are relatively intolerant to the biochemical milieu of many laboratory samples, and may require processing steps that introduce delays. Further, the extrinsic amplification step introduces the possibility of false negative and positives as well. In turn, mass spectrometry is limited in recognition by the need to unambiguously recognize peptide signatures that have less inherent distinction from human or environmental material that may be present in a sample.

Accordingly, a need exists for a rapid method of detecting and identifying infectious disease pathogens. More rapid organism identification would permit informed decisions to be made earlier, for example treatment decisions. A test that provides sensitive, specific detection of pathogen types and subtypes in a relatively short time is needed, so that identification is completed in sufficient time to permit effective treatment of an infected person or removing tainted products from the food supply.

SUMMARY

The current disclosure meets the needs outlined above as well as others. This disclosure relates to a method for increasing the hybridization efficiency of a probe and a target RNA in a cell lysate, for example to identify a particular RNA present in the sample corresponding to a particular organism type and/or subtype. In example embodiments, the method includes heating a sample, such as a cell lysate sample, comprising at least one target RNA, such as a tRNA, mRNA or rRNA, at a temperature between about 80° C. and about 95° C. for a time sufficient to interfere with secondary structure of the RNA, wherein the time is short enough, such that the RNA in the sample, such as a cell lysate sample, are not significantly degraded, and wherein the sample comprises a cell lysis buffer comprising a chemical denaturant, for example a chaotropic agent. In example embodiments, to detect a target RNA in a sample, such as a cell lysate, the sample is contacted with at least one detectable probe, such as a labeled probe, designed to specifically hybridize to the target RNA in the cell lysate. Hybridization between the probe and the target RNA is detected. The methods disclosed herein result in an increase in hybridization, and thus sensitivity, relative to the hybridization between the probe and the target RNA in the absence of the heating step.

In some embodiments of the method, the chemical denaturant in the lysis buffer includes a guanidine salt, such as guanidine isothiocycanate. In some example embodiments of the method, the lysis buffer includes an RNAse inactivator, for example to reduce the possibility of RNA degradation, for example during heating and/or hybridization. Examples of useful RNA inactivators include mercaptans and metal chelation agents among others.

In some specific embodiments of the disclosed method, the sample, such as a cell lysate sample is contacted with a second set of probes, wherein the second set of probes contains at least one second detectable probe that is specific for the target RNA and wherein the individual probes bind to substantially the same region of the RNA as the first set of probes, but wherein the second set of probes do not overlap in sequence identity.

These and other aspects, objects, features, and advantages of the example embodiments will become apparent to those having ordinary skill in the art upon consideration of the following detailed description of illustrated example embodiments.

DETAILED DESCRIPTION OF SEVERAL EMBODIMENTS

I. Summary of Terms

Figure 1:
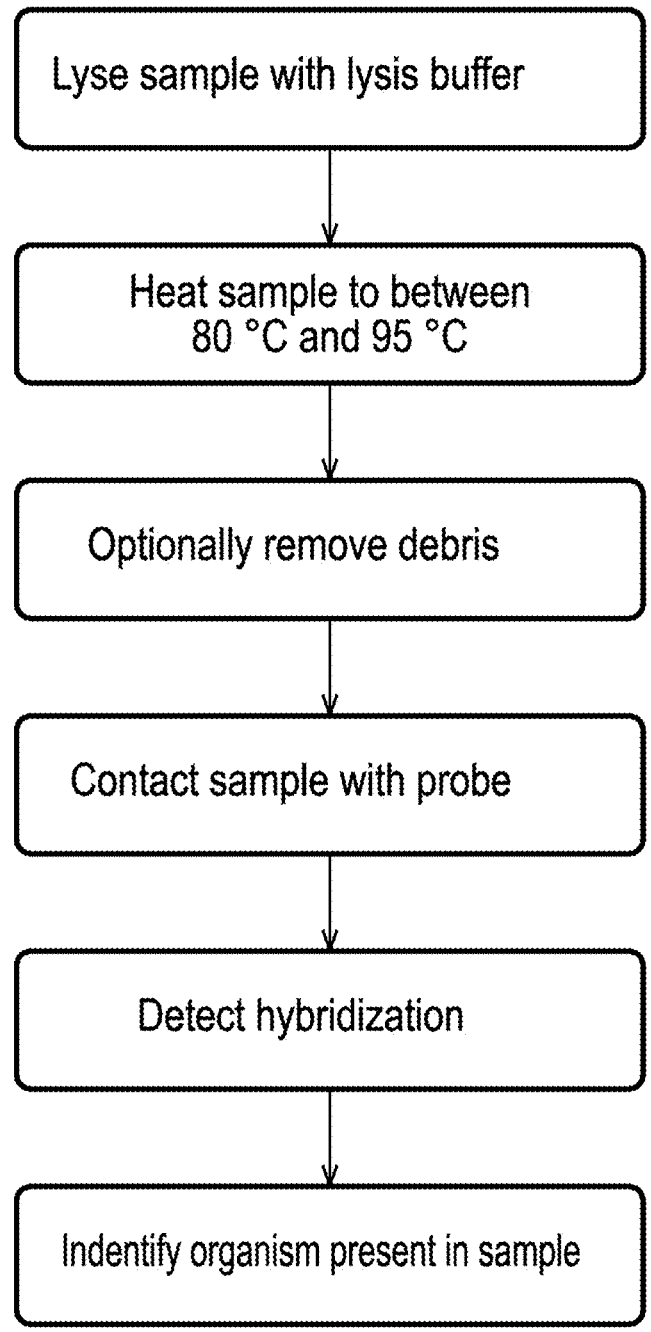
FIG. 1 is a diagram showing an exemplary workflow for an exemplary method of detecting a target RNA in a sample cell lysate.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals. The term mammal includes both human and non-human mammals. Similarly, the term "subject" includes both human and veterinary subjects.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR, reverse transcriptase PCR, real-time reverse transcriptase PCR (rt RT-PCR), nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Binding or stable binding (of an oligonucleotide): An oligonucleotide, such as a probe specific for a target RNA, binds or stably binds to a target RNA if a sufficient amount of the oligonucleotide forms base pairs or is hybridized to its target nucleic acid. Binding can be detected by either physical or functional properties. In some embodiments, a targeting probe stably binds a target nucleic acid under denaturing conditions, for example conditions of high salt, heat and/or chaotropic agents.

Bacterial pathogen: A bacteria that causes disease (pathogenic bacteria). Examples of pathogenic bacteria that can be detected using the methods disclosed herein include without limitation any one or more of (or any combination of) *Acinetobacter baumanii, Actinobacillus* sp., Actinomycetes, *Actinomyces* sp. (such as *Actinomyces israelii* and *Actinomyces naeslundii*), *Aeromonas* sp. (such as *Aeromonas hydrophile, Aeromonas veronii* biovar *sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), Erysipelothrix rhusiopathiae, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (*such as Neisseria gonorrhoeae* and *Neisseria meningitidis*), *Pasteurella multocida*, *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (*formerly: Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others. In some embodiments, the methods disclosed herein can be used to detect a particular bacteria, for example to diagnose a particular bacterial infection or the presence of a bacteria in an environmental sample, or a food product.

Binding site: A region on a protein, DNA, or RNA to which other molecules stably bind. In one example, a binding site is the site on a RNA molecule, such as a target RNA, for example a binding site for a probe.

Change: To become different in some way, for example to be altered, such as increased or decreased. A detectable change is one that can be detected, such as a change in the intensity, frequency or presence of an electromagnetic signal, such as fluorescence. In some examples, the detectable change is a reduction in fluorescence intensity. In some examples, the detectable change is an increase in fluorescence intensity.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-AUCG-3' of one RNA molecule can bond to 3'-UAGC-5' of another RNA to form a dsRNA. In this example, the sequence 5'-AUCG-3' is the reverse complement of 3'-UAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Contacting: Placement in direct physical association, including both in solid or liquid form, for example contacting a sample with a probe, such as a probe specific for a target RNA.

Detect: To determine if an agent (such as a signal or particular nucleic acid, for example a target RNA) is present or absent. In some examples, this can further include quantification. For example, use of the disclosed probes in particular examples permits detection of a fluorophore, for example detection of a signal from an acceptor fluorophore.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite a donor but not an acceptor fluorophore.

Emission or emission signal: The light of a particular wavelength generated from a fluorophore after the fluorophore absorbs light at its excitation wavelengths.

Excitation or excitation signal: The light of a particular wavelength necessary to excite a fluorophore to a state such that the fluorophore will emit a different (such as a longer) wavelength of light.

Fluorophore: A chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser. Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as, Dabcyl, QSY7 (Molecular Probes), QSY33 (Molecular Probes), BLACK HOLE QUENCHERS™ (Glen Research), ECLIPSE™ Dark Quencher (Epoch Biosciences), IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore). "Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule. Examples of oligonucleotides using FRET that can be used to detect amplicons include linear oligoprobes, such as HybProbes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

Fungal pathogen: A fungus that causes disease. Examples of fungal pathogens that can be detected using the methods disclosed herein include without limitation any one or more of (or any combination of) *Trichophyton rubrum, T menta-grophytes, Epidermophyton floccosum, Microsporum canis,* Pityrosporum *orbiculare (Malassezia furfur), Candida* sp. (such as *Candida albicans*), *Aspergillus* sp. (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*). In some embodiments, the methods disclosed herein can be used to detect a particular fungus, for example to diagnose a particular fungal infection or the presence of a fungus in an environmental sample or food product.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour. Through this process, one can rapidly identify pathogenic organisms in a sample or set of samples.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C.

The ability of complementary single-stranded DNA or RNA to form a duplex molecule (also referred to as a hybridization complex). Nucleic acid hybridization techniques can be used to form hybridization complexes between a probe or primer and a nucleic acid, such as a ribonucleic acid. Hybridization occurs between a single stranded probe and a single stranded target ribonucleic acid. "Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The probes and primers disclosed herein can hybridize under low stringency, high stringency, and very high stringency conditions.

Isolated: An "isolated" biological component (such as a protein, a nucleic acid probe, such as the probes and target nucleic acids described herein) has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic acid (molecule or sequence): A deoxyribonucleotide or ribonucleotide polymer including, without limitation, cDNA, mRNA, tRNA, rRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example, as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to, arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Parasite: An organism that lives inside humans or other organisms acting as hosts (for the parasite). Parasites are dependent on their hosts for at least part of their life cycle. Parasites are harmful to humans because they consume needed food, eat away body tissues and cells, and eliminate toxic waste, which makes people sick. Examples of parasites that can be detected using the methods disclosed herein include without limitation any one or more of (or any combination of) Malaria (*Plasmodium falciparum, P. vivax, P. malariae*), Schistosomes, Trypanosomes, *Leishmania*, Filarial nematodes, Trichomoniasis, Sarcosporidiasis, *Taenia* (*T. saginata, T. solium*), *Leishmania, Toxoplasma gondii*, Trichinelosis (*Trichinella spiralis*) or Coccidiosis (*Eimeria* species). In some embodiments, the methods disclosed herein can be used to detect a particular parasite, for example to diagnose a particular parasitic infection or the presence of a parasite in an environmental sample or food product.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions. The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure, include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: A probe comprises an isolated nucleic acid capable of hybridizing to a target nucleic acid (such as a pathogen RNA). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally about 15 nucleotides in length to about 160 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the target nucleic acid molecule, such as 50-140 nucleotides, 75-150 nucleotides, 60-70 nucleotides, 30-130 nucleotides, 20-60 nucleotides, 20-50 nucleotides, 20-40 nucleotides, 20-30 nucleotides, or 40 to 60 nucleotides.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a nucleic acid molecule: Determining or measuring a quantity (such as a relative quantity) of nucleic acid molecule present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence occurs when a quencher molecule (such as fluorescence quenchers listed above) is present in sufficient proximity to the fluorophore that it reduces the fluorescence signal.

Figure 4:
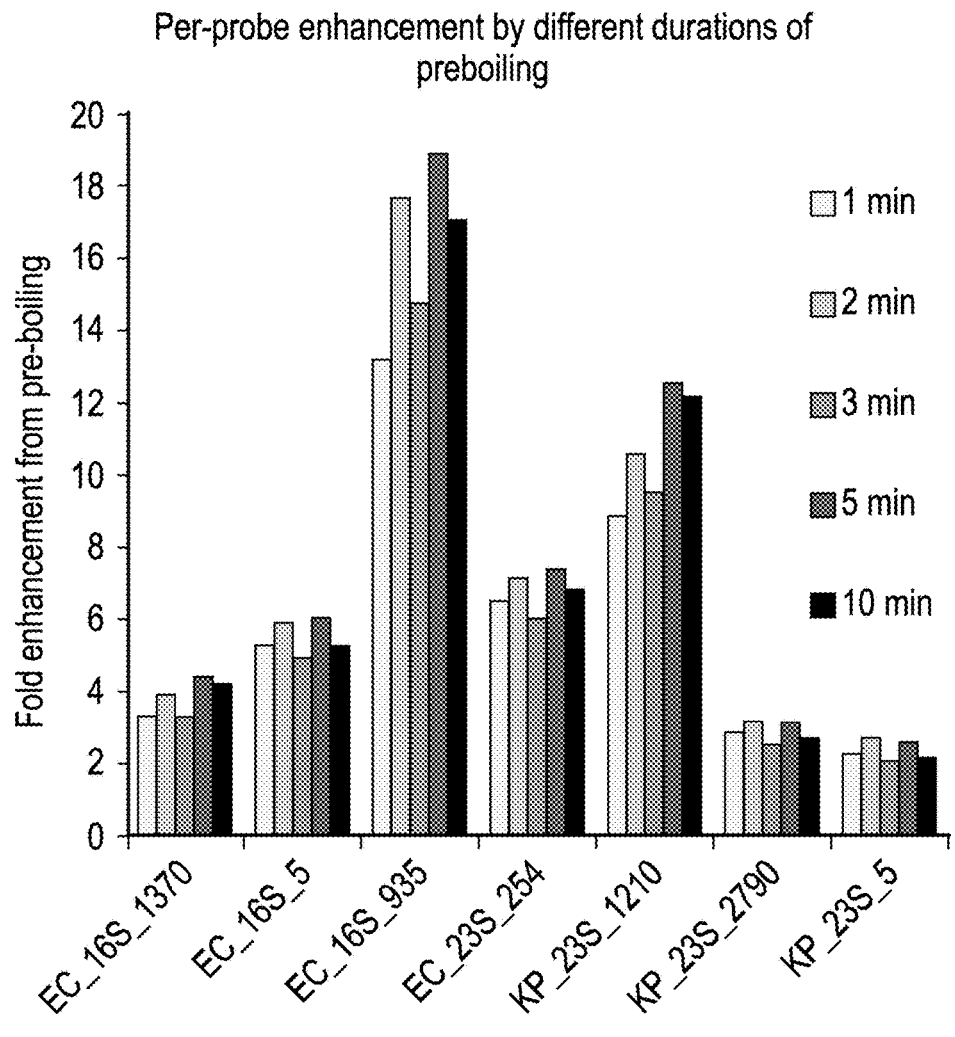
FIG. 4 is a bar graph showing that the percent enhancement of a particular probe is unaffected by prolonged heating.

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid and/or quantitate the initial amounts of a target nucleic acid sequence. In some examples, real time PCR is real time reverse transcriptase PCR (rt RT-PCR). In some examples, the amount of amplified target nucleic acid (is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification. In some examples the change in fluorescence (dRn) is calculated using the equation $dRn = Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample as illustrated in FIG. 4. With reference to FIG. 4, the threshold value (Ct) is the PCR cycle number at which the fluorescence emission (dRn) exceeds a chosen threshold, which is typically 10 times the standard deviation of the baseline (this threshold level can, however, be changed manually if desired).

Sample: A sample, such as a biological sample, that includes biological materials (such as ribonucleic acids (RNA)) obtained from an organism or a part thereof, such as a plant, animal, bacteria, and the like. In particular embodiments, the biological sample is obtained from an animal subject, such as a human subject. In other embodiments, a sample is a sample obtained from a food product. In another embodiment, a sample is an environmental sample, such as soil, sediment water, or air. Environmental samples can be obtained from an industrial source, such as a farm, waste stream, or water source. A sample is any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated). A sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples a sample is a cell lysate.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, *Adv. Appl. Math.* 2:482, 1981; *Needleman & Wunsch, J. Mol. Biol.* 48:443, 1970; Pearson & Lipman, *Proc. Natl. Acad. Sci. USA* 85:2444, 1988; *Higgins & Sharp, Gene*, 73:237-44, 1988; *Higgins & Sharp, CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215: 403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166=1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15-20*100=75).

One indication that two nucleic acid molecules are closely related is that the two molecules hybridize to each other under stringent conditions. Stringent conditions are sequence-dependent and are different under different environmental parameters.

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light.

Target ribonucleic acid molecule: A ribonucleic acid molecule whose detection, quantitation, qualitative detection, or a combination thereof, is intended. The ribonucleic acid molecule need not be in a purified form. In fact the disclosed methods are particularly suited to the detection of a target RNA in a cell lysate or other non-purified sample. Various other ribonucleic acid molecules can also be present with the target ribonucleic acid molecule. For example, the target ribonucleic acid molecule can be a specific ribonucleic acid molecule. Purification or isolation of the target ribonucleic acid molecule, if needed, can be conducted by methods known to those in the art, such as by using a commercially available purification kit or the like, although the current methods have been developed for use in cell lysates, such as crude cell lysate, for example in rapid diagnostic applications. In one example, a target ribonucleic molecule is a pathogen nucleic acid sequence.

Tissue: A plurality of functionally related cells. A tissue can be a suspension, a semi-solid, or solid. Tissue includes cells collected from a subject such as blood, cervix, uterus, lymph nodes, breast, skin, and other organs.

Under conditions that permit binding: A phrase used to describe any environment that permits the desired activity, for example conditions under which two or more molecules, such as nucleic acid molecules, can bind. In some embodiments, conditions that permit binding are denaturing conditions.

Viral Pathogen: A virus that causes disease. Examples of viral pathogens that can be detected using the methods disclosed herein include without limitation any one or more of (or any combination of); Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus, SARS, and MERS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses (such as human papillomavirus-1, human papillomavirus-18, human papillomavirus-2, human papillomavirus-54, human papillomavirus-61, human papillomavirus-cand90, human papillomavirus RTRX7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B 19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, Noroviruses, bovine herpesviruses including Bovine Herpesvirus (BHV) and malignant catarrhal fever virus (MCFV), among others. In some embodiments, the methods disclosed herein can be used to detect a particular virus, for example to diagnose a particular viral infection or the presence of a virus in an environmental sample or food product.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

II. Overview of Several Embodiments

A. Introduction

Clinically, bloodstream infections come to clinical attention at a time when the bacterial burden is very low, with best estimates in the range of 10 to 100 organisms per mL of blood for many common pathogens. While the number of organisms may be low, the relative abundance of RNA makes it an excellent candidate for early detection of organisms. However, one challenge to RNA-based diagnosis (as opposed to DNA) has been that these RNA molecules have tight secondary structural elements that limit their ability to be recognized by hybridization. In large part because of this challenge, many current efforts at bacterial speciation based on RNA have focused on sequencing of the DNA gene that encodes the RNA. This approach typically requires PCR amplification of the gene in question and therefore suffers the same limitations as other PCR-based clinical diagnostics, for example the interdiction of replication errors and increased time to identification. The current disclosure solves those problems by providing an improved method of identifying an organism directly from a cell lysate sample, which increase the speed in which a laboratory diagnostic can be performed, for example from multiple hours to an hour or less. An exemplary methodology of the disclosed method is shown in FIG. 1. The methods disclosed herein are particularly suited to improving the detection of pathogens in a host, such as viral, bacterial, fungal and/or parasitic pathogens, by improving the detection of the RNA from these organisms, see for example Barczak et al. *PNAS, USA,* 109(16), pp. 6217-6222.

B. Exemplary Methods

Disclosed herein is a method of increasing the hybridization efficiency of a probe and a target RNA (such as an ribosomal RNA (rRNA), transfer RNA (tRNA), or messenger RNA (RNA)) in a cell lysate. The disclosed method includes heating a sample, such as a cell lysate sample, comprising at least one target RNA to a temperature of about 80° C. and about 95° C. for a time sufficient to interfere with, for example disrupt, secondary structure of the RNA, wherein the time is short enough, such that the RNA in the cell lysate sample are not significantly degraded in which the cell lysate includes a cell lysis buffer that has a chemical denaturant. Although not bound by theory, the heating step in the presence of a chemical denaturant is believed to make regions of RNA more accessible to a probe, by removing interfering proteins and secondary and/or tertiary elements from the target RNA. In exemplary embodiments of the disclosed method, the samples, such as a cell lysate sample, is contacted with at least one detectable probe that specifically hybridizes to the target RNA in the sample. In example embodiments, the sample is not allowed to cool appreciably before contact with the probe, such that the RNA present in the sample is not allowed to reanneal and form secondary structure that may interfere with probe binding. Hybridization is detected between the probe and the target RNA, which thereby detects the RNA in the sample and hence the organism present in sample, or at least prior to lysis. As is disclosed herein, and shown in the Examples section, heating the sample to temperature of between about 80° C. and about 95° C. for a time sufficient to interfere with secondary structure of the RNA increases the detected hybridization between the probe and the target RNA relative to the hybridization between the probe and the target RNA in the absence of the heating step. In some embodiments, hybridization between the probe and the target RNA detects the presence of the target RNA in the sample. In some embodiments, the samples, such as a cell lysate sample, is contacted with a second set of probes, wherein the second set of probes contains at least one second detectable probe that is specific for the target RNA and wherein the individual probes bind to substantially the same region of the RNA as the first set of probes, but wherein the second set of probes do not overlap in sequence identity.

In some embodiments, the sample, such as a cell lysate sample, is heated to between about 80° C. and about 95° C. to substantially disrupt the secondary structure of the target RNA, for about 1 to about 10 minutes, although longer times can be used. In some examples, the cell lysate is heated to at least 80° C. but less than 95° C., such as about 80° C., about 81° C., about 82° C., about 83° C., about 84 C, about 85° C., about 86° C., about 87° C., about 88° C., about 89° C., about 90° C., about 91° C., about 92° C., about 93° C., about 94° C., or about 95, for example between about 80° C. and about 90° C., about 85° C. and about 90° C., about 80° C. and about 90° C., about 85° C. and about 94° C., or about 87° and about 95° C. Typically, heating conditions are present for a time period sufficient to limit or otherwise reduce non-specific interaction, and/or reduce secondary structure elements in nucleic acids and/or proteins, while at the same time ensuring high yields of the target RNA, for example the sample is not heated for so long as to appreciably degrade the RNA present in the sample. In some examples, the sample, such a cell lysate sample, is heated for between about 1 minute and 10 minutes or even longer, such as about 1 minute, 2, minutes, 3 minutes, 4 minutes, 5 minutes, 6 minutes, 7 minutes, 8 minutes, 9 minutes, 10 minutes or even longer, such as between about 1 minute and about 5 minutes, about 2 minutes and about 8 minutes, about 5 minutes about 10 minutes or about 4 minutes and about 15 minutes.

In some embodiments, the lysate contains a cell lysis buffer that includes a chaotropic agent, such as but not limited to a chemical denaturant, for example guanidinium thiocyanate, guanidinium hydrochloride, urea, and formamide, or any combination thereof. In specific embodiments, the chaotropic agent comprises a guanidine salt, for example guanidine isothiocycanate. In some examples, the lysis buffer includes between about 1M and about 6M chaotropic agent, such as about 1M, about 1.1M about 1.2M, about 1.3M, about 1.4M, about 1.5M, about 1.6M, about 1.7M, about 1.8M, about 1.9M, about 2.0M, about 2.1M about 2.2M, about 2.3M, about 2.4M, about 2.5M, about 2.6M, about 2.7M, about 2.8M, about 2.9M, about 3M, about 3.1M about 3.2M, about 3.3M, about 3.4M, about 3.5M, about 3.6M, about 3.7M, about 3.8M, about 3.9M, or about 4.0M, about 4.1M about 4.2M, about 4.3M, about 4.4M, about 4.5M, about 4.6M, about 4.7M, about 4.8M, about 4.9M, about 5.0M, about 5.1M, about 5.2M, about 5.3M, about 5.4M, about 5.5M, about 5.6M, about 5.7M, about 5.8M, about 5.9M, or about 6.0M chaotropic agent. In some examples, the lysis buffer includes between about 1M and about 5M guanidinium thiocyanate and/or guanidinium hydrochloride, such as about 1M, about 1.1M about 1.2M, about 1.3M, about 1.4M, about 1.5M, about 1.6M, about 1.7M, about 1.8M, about 1.9M, about 2.0M, about 2.1M about 2.2M, about 2.3M, about 2.4M, about 2.5M, about 2.6M, about 2.7M, about 2.8M, about 2.9M, about 3M, about 3.1M about 3.2M, about 3.3M, about 3.4M, about 3.5M, about 3.6M, about 3.7M, about 3.8M, about 3.9M, or about 4.0M, about 4.1M about 4.2M, about 4.3M, about 4.4M, about 4.5M, about 4.6M, about 4.7M, about 4.8M, about 4.9M, or about 5.0M guanidinium thiocyanate and/or guanidinium hydrochloride, for example between about 1.5 and 3.5M guanidinium thiocyanate and/or guanidinium hydrochloride. In some examples, the lysis buffer includes between about 10% and about 70% formamide, such as about 10%, about 15%, about 20%, about 25%, about 30%, about 35%, about 40%, about 45%, about 50%, about 55%, about 60%, or about 70% formamide, for example between about 20% and 50% formamide. In some examples, the lysis buffer includes between about 0M and 1M salt, such as about 0.1M, about 0.2M about 0.3M, about 0.4M, about 0.5M, about 0.6M, about 0.7M, about 0.8M, about 0.9M, or about 1.0M salt.

In some embodiments, the lysis buffer includes one or more agents that substantially inactive any RNAses that may be present in the cell lysate, for example to reduce the possibility of RNA degradation. In some embodiments, an RNAse inactivator includes a mercaptan, such as β-mercaptoethanol, dithiothreitol and the like, which covalently bond to cysteine residues in the active site of an RNAse, thus inactivating the enzyme. In some embodiments, an RNAse inactivator includes a metal chelation agent, such as EDTA, EGTA and the like, which remove metal ions from the active sites of metal dependent RNAses, thus inactivating the enzyme.

In some embodiments, after heating the denatured protein and other cellular debris is removed from the sample, for example using centrifugation, prior to contacting the sample, such as cell lysate sample, with the probe to detect target RNA in the sample.

In some embodiments, the temperature of the sample is maintained at least 65° C. but less than 95° C. prior to contact with the probe, for example between the heating step and the contacting step, such as at least about 65° C., at least about 66° C., at least about 67° C., at least about 68° C., at least about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C. about 86° C., about 87° C., about 88° C., about 89° C., about 90° C., about 91° C., about 92° C., about 93° C., about 94° C., or about 95, for example between about 65° C. and about 80° C., about 85° C. and about 90° C., about 65° C. and about 90° C., about 70° C. and about 83° C., or about 70° and about 75° C.

As disclosed herein, the target RNA can be any RNA that allows the detection of an organism, for example using a probe that is specific for the target RNA. In some embodiments at least one target RNA comprises target ribosomal RNA (rRNA). In some embodiments at least one target RNA comprises target messenger RNA (mRNA). In some embodiments at least one target RNA comprises target transfer RNA (tRNA).

In example embodiments of the disclosed method, nucleic acid probes and provided for the detection of and discrimination between organisms. The probes can be composed of RNA, DNA or a combination thereof, including synthetic nucleotides. Typically the probes are between 15 and 160 nucleotides in length, such 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the target nucleic acid molecule, such as 50-140 nucleotides, 75-150 nucleotides, 60-70 nucleotides, 30-130 nucleotides, 20-60 nucleotides, 20-50 nucleotides, 20-40 nucleotides, 20-30 nucleotides, or 40-60 nucleotides and capable of hybridizing to a target RNA sequence. In some embodiments, the probes are specific for a target RNA sequence from an organism at the exclusion of other organisms. In some embodiments, the probes are specific for a target tRNA sequence from an organism at the exclusion of other organisms. In some embodiments, the probes are specific for a target mRNA sequence from an organism at the exclusion of other organisms. The probes can be selected by determining at least one detectable probe that is specific for a target RNA sequence of each species, the determination comprising determining shared RNA sequences between members of each of the two or more species; determining divergent RNA sequences between each of the two or more species of the one or more organisms, wherein the divergent RNA sequences share about 85% or less sequence identity, such as less than about 80%, less than about 75%, less than about 70%, or even less than about 50% identity, to identify a target RNA sequence for each species; and, designing a probe for the target RNA sequence of each species that specifically binds to the shared RNA sequences between members of a given species, wherein the individual probes for are each species are about 85% or less identical, such as less than about less than about 75%, less than about 70%, or even less than about 50% identical. In certain example embodiments, the divergent RNA sequences share about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

In some embodiments, the probe is detectably labeled, either with an isotopic or non-isotopic label, alternatively the target ribonucleic acid is labeled. Non-isotopic labels can, for instance, comprise a fluorescent or luminescent molecule, biotin, an enzyme or enzyme substrate or a chemical. Such labels are preferentially chosen such that the hybridization of the probe with target ribonucleic acid (such as a ribonucleic acid from a pathogen) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase. Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.)

beads. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149; and U.S. Pat. No. 4,366,241. In some embodiments, a disclosed probe is labeled. In some embodiments, the probes are differentially labeled, for example with different reports, so that the probes may be used in multiplex assay. In specific embodiment the probe is radiolabeled, fluorescently-labeled, biotin-labeled, enzymatically-labeled, or chemically-labeled. In some embodiments, the label comprises a capture moiety, such as biotin. In some embodiments, the probe is attached to a solid surface. In some embodiments, a disclosed probe is labeled. I some embodiments, the probes are differentially labeled, for example with different reports, so that the probes may be used in multiplex assay. In specific embodiment the probe is radiolabeled, fluorescently-labeled, biotin-labeled, enzymatically-labeled, or chemically-labeled. In some embodiments, the label comprises a capture moiety, such as biotin.

In some embodiments, the disclosed method is used to detect the presence of a pathogen in a sample, such as a biological sample obtained from a subject or in an environmental or food product or material that will become a food product, such as meat, poultry or plant. The disclosed methods are particularly suited to identify bacterial species based on annealing to the target RNA (such as mRNA, tTNA and rRNA) present in a sample.

The present method allows the detection of pathogens and distinguishing between two or more species of one or more organisms, e.g., bacteria, yeast, parasites, viruses, and fungi or a combination thereof, in a biological sample, by detecting the hybridization between the sample containing the target RNA (such as mRNA, tTNA and rRNA) and one or more antisense probes, wherein the probes contain at least one detectable probe that is specific for a target RNA sequence of the species to be tested.

Disclosed herein are methods for distinguishing between two or more species of one or more organisms in a sample. The methods or also amenable to detecting one or more species of one or more organisms in a sample.

The method comprises, for example, contacting a sample comprising the target RNA (such as mRNA, tTNA and rRNA), such as a sample obtained from a subject, such as a human subject, or an environmental sample, or food source sample, with a set of probes that are antisense, e.g. anneal to a target or set of target RNAs. The set of probes comprises at least one detectable probe that is specific for a target RNA sequence of each species to be tested, wherein the individual probes specific for each species have about 85% or less sequence identity to the probes for the other species, such as less than about 75%, less than about 70%, or even less than about 50% sequence identity to the probes for the other species. The method further comprises detecting hybridization between one or more of the probes and the RNA, thereby distinguishing between two or more species in a sample. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

Hybridization between one or more of the probes and the target RNAs is detected, thereby distinguishing between two or more species in a sample. In some embodiments, detecting hybridization between the probe indicates the presence of the species in the sample, and can indicate that the subject from which, the sample was obtained is infected and/or contaminated with the organism. In some embodiments, the organisms include, or consist of, one or more microorganisms, for example, bacteria, yeast, and fungi or a combination thereof. In some examples the one or more microorganism include one or more human pathogens.

By way of example the sequences of annotated 16S rRNA-encoding genes are extracted from the NCBI database of fully sequenced bacterial genomes. 16S rRNA sequences derived from all strains of interest are examined to identify conserved regions among strains of the same species but significantly divergent among different species. These regions are then targeted for hybridization-based detection, for example using Nanostring's method of two DNA oligonucleotides that bind to adjacent 50-nucleotide stretches of RNA. When the target transcript is present in a lysate, it links a biotinylated DNA oligo (the "capture probe") to an adjacent fluorescently labeled DNA oligo (the "reporter probe").

In particular embodiments, two molecular probes are added to a crude sample lysate. A capture probe comprises 50 nucleotides complementary to a given RNA molecule, and can be conjugated to biotin. A reporter probe comprises a different 50 nucleotides complementary to a different part of the same RNA molecule, and can be conjugated to a reporter molecule, e.g., a fluorescent tag or quantum dot. Each reporter probe uniquely identifies a given RNA molecule. The capture and reporter probes hybridize to their corresponding RNA molecules within the lysate. Excess reporter is removed by bead purification that hybridizes to a handle on each oligomer, leaving only the hybridized RNA complexes. The RNA complexes can be captured and immobilized on a surface, e.g., a streptavidin-coated surface. An electric field can be applied to align the complexes all in the same direction on the surface before the surface is microscopically imaged.

In some embodiments, the technique employs a commercial RNA recognition technology known as NanoString, which has largely been applied to characterization of messenger RNA (mRNA) transcripts. The reporter probes can be counted to provide a quantitative measure of RNA molecules. A commercially available nCounter® Analysis System (NanoString, Seattle, Wash.) can be used in the procedure. It will be understood by those skilled in the art, that other systems may be used in the process.

In some embodiments of the disclosed methods, determining the identity of a nucleic acid includes detection by nucleic acid hybridization. Nucleic acid hybridization involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, Methods in Molecular Biology 106:247-283, 1999); RNase protection assays (Hod, Biotechniques 13:852-4, 1992); and PCR-based methods, such as reverse transcription polymerase chain reaction (RT-PCR) (Weis et al., *Trends in Genetics* 8:263-4, 1992).

In some examples, nucleic acids are identified or confirmed using the microarray technique.

Means of detecting such labels are also well known. Thus, for example, radiolabels may be detected using photographic film or scintillation counters. Fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

Appropriate samples for use in the methods disclosed herein include any conventional biological sample obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis).

A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984).

In certain embodiment, for example as relates to monitoring the food supply, the sample is a food product. Examples of food products include, without limitation, plant matter such as fresh fruits, vegetables, nuts, grains, and cereals or animal matter such as fish, beef, pork, fowl, and the like. The food product can also be a commodity, which refers to a food product that has not been processed into other products or product forms, but may have been subjected to typical picking and packing processes, including washing and packaging. In some examples, a sample is an environmental sample.

In another embodiment, a detectable probe that is specific for a target RNA sequence of a species is determined, wherein the determination comprises: determining shared RNA sequences between members of each of the two or more species; determining divergent RNA sequences between each of the two or more species, wherein the divergent RNA sequences share about 85% or less sequence identity, to identify a target RNA sequence for each species; and, designing a probe for the target RNA sequence of each species that specifically binds to the shared rRNA sequences between members of a given species, wherein the individual probes for are each species are about 85% identical. In certain example embodiments, the divergent RNA sequences share about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

Several embodiments of the present disclosure involve the use of procedures and approaches known in the art to successfully fractionate clinical blood samples. See, e.g. the procedure described in Han Wei Hou et al., *Microfluidic Devices for Blood Fractionation*, Micromachines 2011, 2, 319-343; Ali Asgar S. Bhagat et al., *Dean Flow Fractionation (DFF) Isolation of Circulating Tumor Cells (CTCs) from Blood*, 15th International Conference on Miniaturized Systems for Chemistry and Life Sciences, Oct. 2-6, 2011, Seattle, Wash.; and International Patent Publication No.

WO2011109762, the disclosures of which are herein incorporated by reference in their entirety.

Further, several embodiments of the present disclosure involve the use of procedures and approaches known in the art to successfully isolate pathogens from whole blood using spiral microchannel, as described in Han Wei Hou et al., International Patent Publication No. WO2014/152643, published Sep. 25, 2014, the disclosure of which is herein incorporated by reference in its entirety.

In some embodiments, the probe is attached to a solid surface, for example as part of an array.

An array containing a plurality of heterogeneous probes for the detection of, and discrimination between, organisms, such as pathogenic microorganisms are disclosed. Such arrays may be used to rapidly detect, and discriminate between, organisms in a sample.

Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, an organism profiling array is a collection of separate probes at the array addresses. The organism profiling array is then contacted with a sample suspected of containing RNA from one or more organisms under conditions allowing hybridization between the probe and nucleic acids in the sample to occur. Any sample potentially containing, or even suspected of containing, RNA from one or more organisms may be used, including nucleic acid extracts or lysates. A hybridization signal from an individual address on the array indicates that the probe hybridizes to a nucleotide within the sample. This system permits the simultaneous analysis of a sample by plural probes and yields information identifying the rRNA from one or more organisms contained within the sample. In alternative embodiments, the array contains rRNA from one or more organisms and the array is contacted with a sample containing a probe. In any such embodiment, either the probe or the RNA acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

RNA profiling arrays may vary in structure, composition, and intended functionality, and may be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

The nucleic acid probes disclosed herein can be supplied in the form of a kit for use in detection of, and discrimination between, organisms, such as pathogenic microorganisms, including kits for any of the arrays described below. In such a kit, an appropriate amount of one or more of the nucleic acid probes is provided in one or more containers or held on a substrate. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of, and discrimination between, organisms, such as pathogenic microorganisms.

In some applications, one or more probes may be provided in pre-measured single use amounts in individual, typically disposable, tubes or equivalent containers. With such an arrangement, the sample to be tested can be added to the individual tubes.

The amount of nucleic acid probe supplied in the kit can be any appropriate amount, and may depend on the target market to which the product is directed. General guidelines for determining appropriate amounts may be found in Innis et al., Sambrook et al., and Ausubel et al.

Particular embodiments include a kit for detection of, and discrimination between, organisms, such as pathogenic microorganisms. Such a kit includes at least one probe specific for an RNA and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample.

In some embodiments, a kit for detecting a bacterial ribosomal ribonucleic acid in a sample is described, wherein the kit contains a probe disclosed herein and instructions for hybridizing the probe to a bacterial ribosomal ribonucleic acid from a biological sample.

The following examples are provided to illustrate certain particular features and/or embodiments. These examples should not be construed to limit the invention to the particular features or embodiments described.

EXAMPLES

Example 1

This example demonstrates that the disclosed methods increase the hybridization efficiency of nucleic acid probes for rRNAs present in a cell lysate.

Cells are grown under desired conditions for analysis. A lysis buffer (eg, the guanidinium-containing Qiagen RLT buffer) is added in 1× to 5× volume and mixed vigorously to lyse cells. If necessary for lysis efficiency, cells may be bead-beaten in this buffer. Separately, the hybridization buffer (such as that supplied by Nanostring) is mixed with water and the reporter probeset (eg, the fluorescently labeled mixture of probes complementary to a desired set of target mRNAs) to make "mixture A". Mixture A is then equilibrated at 65° C. on a pre-heated thermocycler for up to 5 minutes. An aliquot of each lysate to be analyzed is then either incubated at 95° C. on a pre-heated thermocycler for 2 minutes (may vary from 1 to 10 minutes), or not, and then added immediately to the pre-equilibrated mixture A at 65° C., using a multichannel pipetman to ensure rapid and simultaneous addition, to make "mixture B", which remains at 65° C. without cooling to prevent re-formation of secondary structure in the RNA species present in the lysate. The capture probeset (eg, the biotinylated mixture of probes complementary to an adjacent region of the desired set of target mRNAs) is then added to mixture B at 65° C., and incubation is allowed to proceed on the thermocycler at 65° C. for the various lengths of time as described. Once the hybridization step is complete, the samples are processed by immobilizing the capture probes and detecting the reporter probes (eg, loaded on a Nanostring nCounter Prep Station, then read on a Nanostring nCounter Digital Analyzer per manufacturer's protocol).

Figure 2:
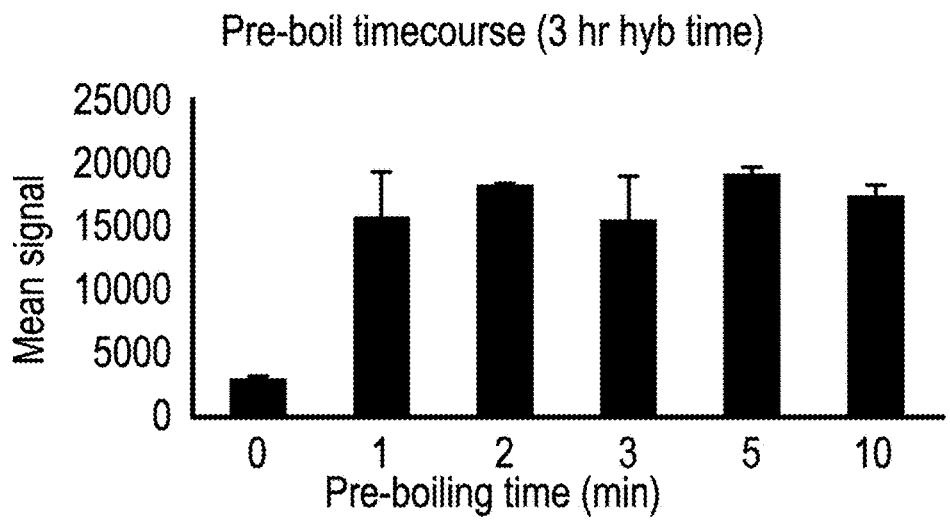
FIG. 2 is a bar graph showing the mean hybridization signal obtained for different heating times. This data demonstrates that the heating step increase hybridization efficiency as measured by hybridization of a target RNA with a probe specific for the target RNA.

As shown FIG. 2, using a prehybridization boiling (or heating step) of 95° C. improves signal after 1 minute. The improvement in signal is robust to different pre-boiling times for ribosomal RNA. For example 1, 2, 3, 5, and 10 minutes of boiling were roughly equivalent, and all provided roughly 5× increase in signal after 2 hours of hybridization. In other words, even by 10 minutes, there was not significant degradation of RNA from cell lysates treated at 95° C. degrees in guanidine-containing lysis buffer.

Figure 3:
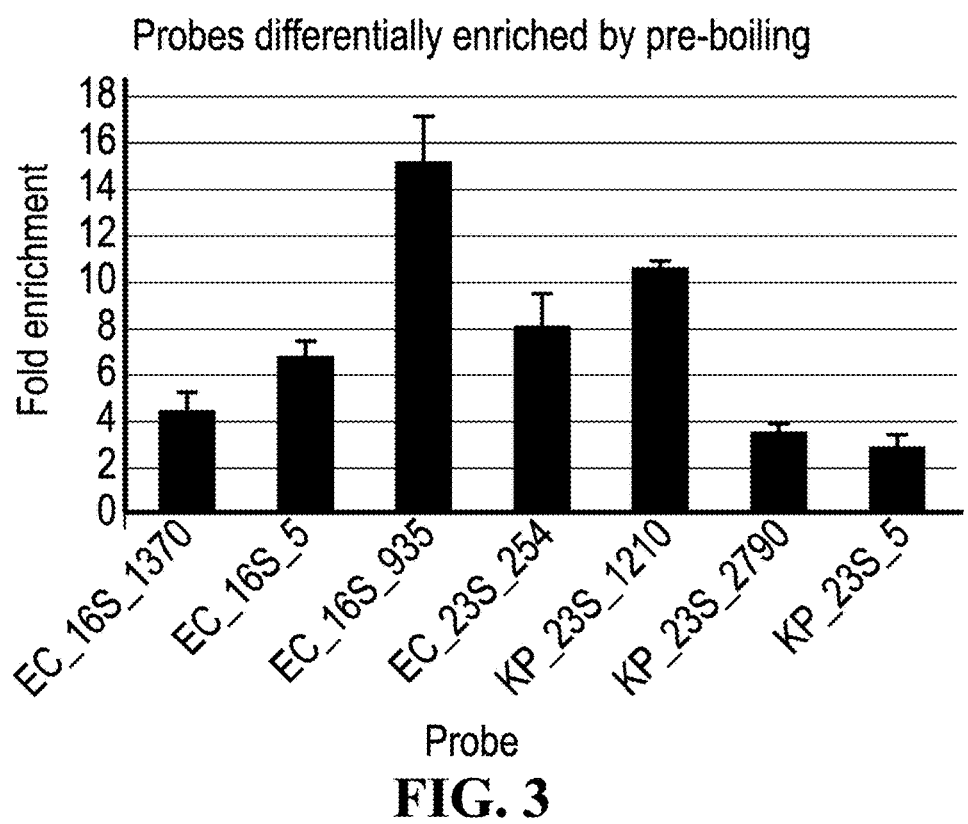
FIG. 3 is a bar graph showing that different probes are differentially enriched by preheating in a hybridization assay for RNA detection.

Although, there was an overall increase in the hybridization efficiency, there is some variability from probe to probe in terms of degree of signal enhancement by pre-boiling; all probes tested exhibited an enhancement of at least 2.5 fold. As shown in FIG. 3, this variability ranges from 2.5× to 15× for the above experiment in which the mean enhancement for all probes is 5×. The variability in signal enhancement is also reproducible across experiments—i.e., for the same set of 7 probes, each shows roughly the same degree of enhancement in multiple different experiments, reproducible for an exemplary rRNA probeset. Similar results were obtained with an exemplary mRNA probe set.

During testing, it was discovered that the disclosed methods increase the hybridization efficiency on cell lysates not total RNA, which is independent of the presence of lysis buffer. For example dilution of purified total RNA in lysis buffer, preboiling does not seem to improve signal. This is in contrast to the situation in cells.

Figure 5A:
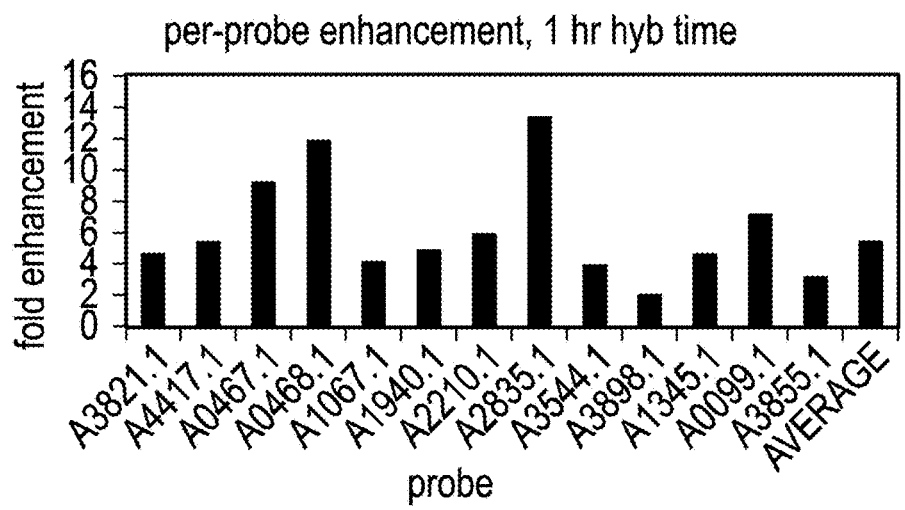
FIGS. 5A and 5B are a set of bar graphs showing that per probe enhancement above a non-preheated baseline does not appreciably increase after one hour of hybridization.
Figure 5B:
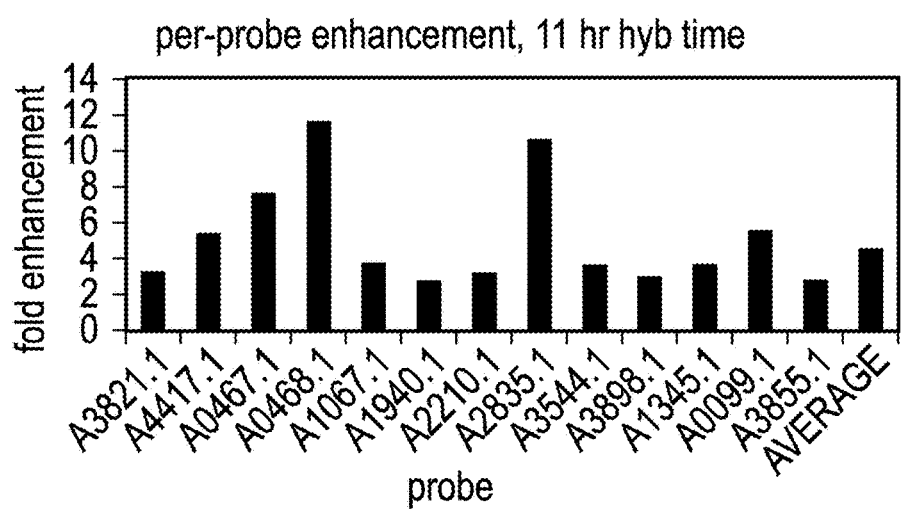
Figure 6:
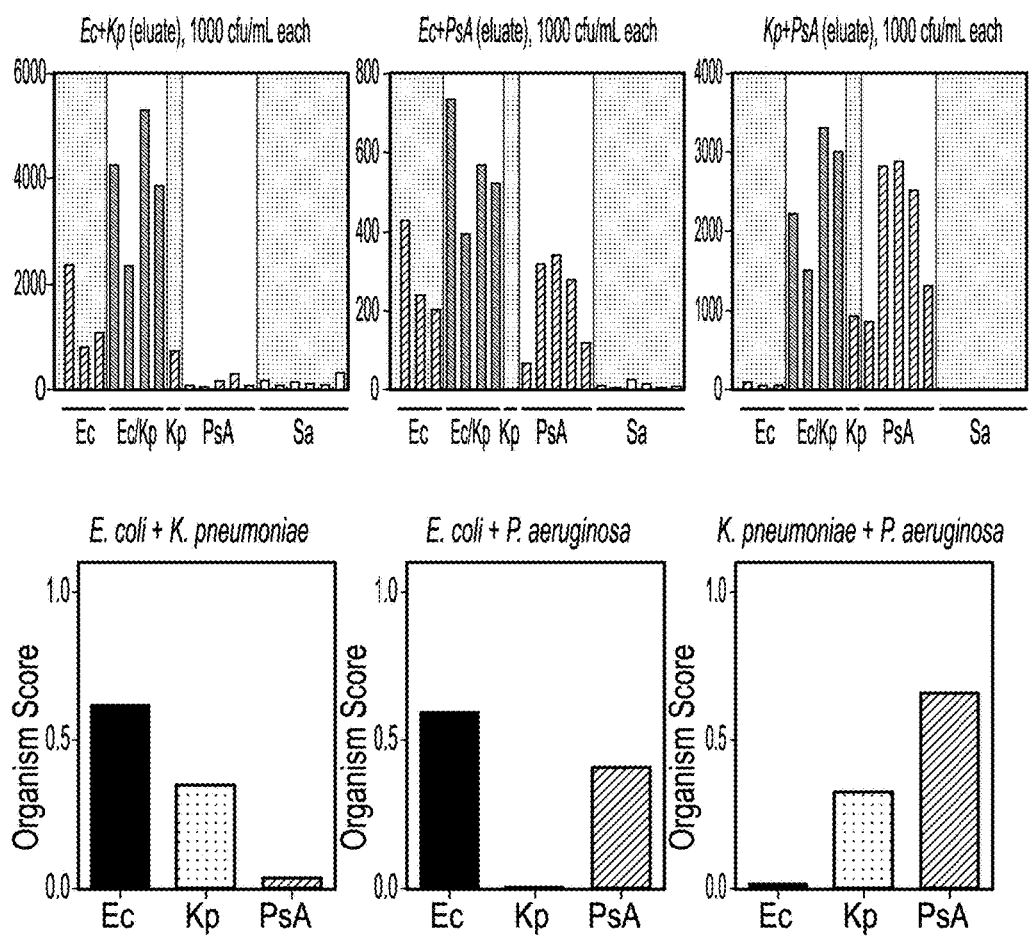
FIG. 6 shows the detection of pathogens in multiple combinations by rRNA recognition using the. Each of the 3 possible pairwise combinations of *E. coli, K. pneumoniae*, and *P. aeruginosa* were inoculated into whole blood at 1000 cfu/mL, processed by Dean Flow fractionation for bacterial enrichment, and concentrated before being detected by the NanoString® rRNA detection assay with pre-treatment as described (heating to 95° C.×2 min) prior to hybridization. Top panel: each probe's value is displayed; first 3 probes (blue, Ec) recognize *E. coli* only, next 4 probes (purple, Ec/Kp) recognize either *E. coli* or *K. pneumonaie*, next probe (red; Kp) recognizes *K. pneumoniae* only, next 5 probes recognize *P. aeruginosa* only, and last 6 probes (yellow, PsA) recognize *S. aureus* only (which was not included in this experiment). Bottom panel: probe values from the top panel are combined into a single Organism Score to more clearly reflect which organisms were detected in each mixture. Ec=*E. coli*, Kp=*K. pneumoniae*, PsA=*P. aeruginosa*.

As shown in FIG. 4 (rRNA probes, from *E coli* cell lysate, boiling time as shown, hyb time 2 hrs), per-probe enhancement by boiling at different boiling times reaches a maximum at 1 minute. In addition, as show in FIGS. 5A and 5B (mRNA probes, from *E coli* cell lysate, boiling time 2 minutes, hyb time as shown), per-probe enhancement by boiling at different appear independent of hybridization time, demonstrating that the disclosed methods can produce robust results in a short period of time, which is particularly amenable to diagnostic applications that need to be accomplished quickly.

Example 2

Preparation of Probe Sets

This example describes the generation of probe sets for the detection and discrimination of pathogenic organisms in a sample, with particular reference to *Escherichia coli* and *Klebsiella pneumoniae*

Sequence data from closely related organisms was analyzed and aligned to see if there were any stretches of 100 nucleotides with sufficient sequence divergence to allow for selective hybridization. For even the most-related organisms, *Escherichia coli* and *Klebsiella pneumoniae*, there were such regions.

Sequences were gathered from every ribosomal RNA gene (up to approximately 5-6 per genome for each subunit) from all sequenced genomes in the NCBI database for the four organisms in the pilot (*Escherichia coli, Klebsiella pneumoniae, Pseudomonas aeruginosa,* and *Staphylococcus*

*aureus*). Of the 23S rRNA sequences, 133 sequences were derived from *Escherichia coli*, 23 from *Klebsiella pneumoniae*, nine from *Pseudomonas aeruginosa*, and 54 from *Staphylococcus aureus*; of the 16S rRNA sequences, 125 were derived from *Escherichia coli*, 21 from *Klebsiella pneumoniae*, eight from *Pseudomonas aeruginosa*, and 55 from *Staphylococcus aureus*; of the 5S rRNA sequences, 68 were derived from *Escherichia coli*, eight from *Klebsiella pneumoniae*, four from *Pseudomonas aeruginosa*, and 31 from *Staphylococcus aureus*.

A list of approximately 520 possible probes was compiled, which was further pared down to 23 non-overlapping probe sequences. Based on the alignments, and due to the similarity between *Escherichia coli* and *Klebsiella pneumoniae* (both species being enteric Gram-negative rods), of the 23 non-overlapping probe sequences, only 3 were from *Escherichia coli* and only one was from *Klebsiella pneumoniae*. Probes that were shared between *Escherichia coli* and *Klebsiella pneumoniae* but distinct from the other species in question we also sought. This resulted in an additional 10 probes that were shared between these two species. Of the resulting 33 possible probes, 23 were chosen that best represented the 4 species and, of these 23 probes that were tested, 19 worked well enough against the 16 clinical isolates tested to include in the final analysis.

Some species share too much homology between their rRNA subunits for this approach to successfully discriminate between them. While this threshold will vary based on the detection technique (such as those based on RT-PCR, like Fluidigm, versus those based on hybridization, like Nanostring), there will eventually be a line beyond which it will be difficult to separate. However, the conceptual approach still allows one to group organisms into classes of similar rRNA sequence. And because organisms with similar rRNA sequences are more closely related (eg, *Escherichia coli* and *Klebsiella pneumoniae* are both enteric Gram-negative rods, whereas *Pseudomonas aeruginosa* is a non-enteric Gram-negative rod and *Staphylococcus aureus* is a Gram-positive coccus), these organisms that group together and may overlap, will behave in a clinically similar manner and typically respond to similar treatments. Thus it may still be of clinical value to identify something early as "*E. coli*-like" or "*Staph aureus*-like", even if unable to identify the exact species.

Experiments Using the Pilot Probeset

Capture and reporter probes were designed that selectively anneal to the 5S, 16S, and 23S rRNA of *Escherichia coli*, *Klebsiella pneumoniae*, *Pseudomonas aeruginosa*, and *Staphylococcus aureus*, four major clinical pathogens. The pathogens were chosen for the pilot study because they cover a broad range of phylogenetic space among pathogenic microbes: two closely related enteric Gram negative bacilli (*E. coli* and *K. pneumoniae*) and a non-enteric Gram negative bacillus (*P. aeruginosa*) of the proteobacteria family, and a Gram positive coccus (*S. aureus*) of the firmicute family. Data from a total of 19 probes that recognize these species was generated and analyzed. The close phylogenetic relationship between the two enteric Gram negative bacilli required that 5 of these probes recognize both *E. coli* and *K. pneumoniae*, although we were also able to generate 3 probes specific to *E. coli* alone, and 1 probe unique to *K. pneumoniae*.

Example 3

Detection of Pathogens in a Sample Obtained from a Subject

This example describes and exemplary procedure for testing a biological sample for a pathogenic organism.

A sample is obtained from a subject suspected of having an infection with one or more pathogenic organisms, such as a fast moving bacterial infection. In some examples, the sample is a blood sample and the sample is fractionated, for example using the procedures and described in Han Wei Hou et al., *Microfluidic Devices for Blood Fractionation*, Micromachines 2011, 2, 319-343; Ali Asgar S. Bhagat et al., *Dean Flow Fractionation (DFF) Isolation of Circulating Tumor Cells (CTCs) from Blood*, 15$^{th}$ International Conference on Miniaturized Systems for Chemistry and Life Sciences, Oct. 2-6, 2011, Seattle, Wash.; and International Patent Publication No. WO2011109762. The sample is lysed with a lysis buffer disclosed herein and heated to 95° C. for 1 to 10 minutes. The sample is centrifuged to remove cellular debris. The cleared cell lysate is contacted with a probe set to screen the sample for multiple pathogenic species and subtypes. Hybridization between RNA and the sample is detected and the organism in the sample is detected. In some examples a treatment for the infection is administered.

Example 4

Detection of Pathogens in Food Product Sample

This example describes and exemplary procedure for testing a food product sample for a pathogenic organism.

A sample is obtained from a food product undergoing testing for pathogen contamination, either as routine testing or specific testing. The sample is lysed with a lysis buffer disclosed herein and heated to 95° C. for 1 to 10 minutes. The sample is centrifuged to remove cellular debris. The cleared cell lysate is contacted with a probe set to screen the sample for multiple pathogenic species and subtypes. Hybridization between RNA and the sample is detected and the organism in the sample is detected. In some examples the food product is removed from the food distribution channels.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of increasing the hybridization efficiency of a probe and a target RNA in a cell lysate, comprising:
heating a cell lysate sample comprising at least one target RNA at a temperature of between 80° C. and 95° C. for a time sufficient to interfere with secondary structure of the RNA, wherein the time is short enough, such that the RNA in the cell lysate sample is not sufficiently degraded to prevent hybridization, and wherein the cell lysate comprises a cell lysis buffer comprising a chemical denaturant;
contacting the cell lysate sample with at least one detectable probe that specifically hybridizes to the at least one target RNA in the cell lysate sample; and
detecting hybridization between the probe and the at least one target RNA, wherein the detected hybridization between the probe and the at least one target RNA is increased at least 2.5 fold relative to the hybridization between the probe and the at least one target RNA in the absence of the heating step; and wherein the at least one target RNA is selected from the group consisting of *Escherichia coli*, *Klebsiella pneumoniae*, *Pseudomonas aeruginosa*, and *Staphylococcus aureus*.

2. The method of claim 1, wherein the lysis buffer comprises a guanidine salt.

3. The method of claim 2, wherein the guanidine salt comprises guanidine isothiocyanate.

4. The method of claim 1, wherein the lysis buffer comprises an RNAse inactivator.

5. The method of claim 4, wherein the RNAse inactivator comprises a mercaptan, or metal chelation agent.

6. The method of claim 5, wherein the mercaptan comprises B-mercaptoethanol.

7. The method of claim 1, further comprising, centrifugation of the sample prior to contacting the cell lysate sample with the probe, to remove denatured protein and other cellular debris.

8. The method of claim 1, wherein the temperature of the sample is maintained at at least 65° C. prior to contact with the probe.

9. The method of claim 1, wherein the at least one target RNA comprises target ribosomal RNA (rRNA), target messenger RNA (mRNA), or a combination thereof.

10. The method of claim 1, wherein the detectable probe is labeled.

11. The method of claim 10, wherein the probe is radiolabeled, fluorescently-labeled, biotin-labeled, enzymatically-labeled, or chemically-labeled.

12. The method of claim 10, wherein the label comprises a capture moiety.

13. The method of claim 12, wherein the capture moiety comprises biotin linked to a nucleotide.

14. The method of claim 1, wherein the probe is attached to a solid surface.

15. The method of claim 1, further comprising:
distinguishing between two or more species of one or more organisms in a sample, comprising:
contacting the sample with a set of probes, wherein the set of probes contains at least one detectable probe that is specific for a target RNA sequence of each species to be tested, and wherein individual probes in the probe set are specific for each species; and
detecting hybridization between one or more of the probes and the RNA, thereby distinguishing between two or more species in the sample.

16. The method of claim 15, further comprising contacting the sample with a second set of probes, wherein the second set of probes contains at least one second detectable probe that is specific for the target RNA and wherein individual probes in the second set of probes bind to substantially the same region of the RNA as the first set of probes, but wherein the second set of probes does not align in sequence with the first set of probes.

17. The method of claim 16, wherein the second detectable probe is labeled.

18. The method of claim 17, wherein the second detectable probe is radiolabeled, fluorescently-labeled, biotin-labeled, enzymatically-labeled, or chemically-labeled.

19. The method of claim 16, wherein the second detectable probe is attached to a solid surface.

20. The method of claim 17, wherein the label comprises a capture moiety.

21. The method of claim 20, wherein the capture moiety comprises biotin linked to a nucleotide.

22. The method of claim 1, wherein the sample is obtained from an animal subject suspected of having an infection with one or more organisms pathogenic to that animal subject.

23. The method of claim 22, wherein the animal subject is a veterinary subject.

24. The method of claim 22, wherein the animal subject is a human subject.

25. The method of claim 1, wherein detecting hybridization between the probe and the RNA indicates the presence of at least one of the two or more species in the sample.

26. The method of claim 25, wherein the presence of at least one of the two or more species indicates the sample is infected or contaminated with the at least one species of organism.

27. The method of claim 1, wherein the sample is obtained from an environmental sample.

28. The method of claim 1, wherein the sample is obtained from a food product or material that will become a food product.

29. The method of claim 28, wherein the material that will become a food product comprises meat, poultry, or plant matter.

* * * * *